United States Patent [19]

Imai et al.

[11] Patent Number: 4,774,028
[45] Date of Patent: Sep. 27, 1988

[54] LIQUID CRYSTALLINE ORGANOSILICON COMPOUNDS

[75] Inventors: Takeshi Imai, Ichihara; Naoyuki Koide, Tokyo, both of Japan

[73] Assignee: Toray Silicone Co., Ltd., Tokyo, Japan

[21] Appl. No.: 737,370

[22] Filed: May 23, 1985

[30] Foreign Application Priority Data

May 28, 1984 [JP] Japan ................. 59-108053

[51] Int. Cl.$^4$ .............. C07J 9/00; C09K 19/36; C09K 19/22; C09K 19/12

[52] U.S. Cl. ............. 260/397.2; 252/299.01; 252/299.6; 252/299.7; 252/299.68; 252/299.66; 252/299.65; 556/416; 556/417; 556/423; 556/439; 556/441

[58] Field of Search ........... 252/299.01, 299.4, 299.66, 252/299.6, 299.65, 299.68, 299.67, 299.7; 428/1; 556/439, 441, 416, 423, 444, 417; 528/25, 26, 28, 29; 260/397.2

[56] References Cited

U.S. PATENT DOCUMENTS

| | | | |
|---|---|---|---|
| 4,316,041 | 2/1982 | Totten et al. | 260/397.2 |
| 4,358,391 | 11/1982 | Finkelmann et al. | 252/299.01 |
| 4,388,453 | 6/1983 | Finkelmann et al. | 252/299.4 |
| 4,410,570 | 10/1983 | Kreuzer et al. | 252/299.01 |
| 4,469,408 | 9/1984 | Kruger et al. | 252/299.4 |
| 4,494,482 | 1/1985 | Totten et al. | 260/397.2 |
| 4,657,694 | 4/1987 | Heeger et al. | 252/299.01 |
| 4,678,283 | 7/1987 | Kreuzer et al. | 252/299.4 |
| 4,702,558 | 10/1987 | Coles et al. | 252/299.66 |
| 4,713,196 | 12/1987 | Praefche et al. | 252/299.01 |
| 4,730,904 | 3/1988 | Pauluth et al. | 252/299.4 |

FOREIGN PATENT DOCUMENTS

| | | | |
|---|---|---|---|
| 121876 | 10/1984 | European Pat. Off. | 252/299.01 |
| 3031126 | 4/1982 | Fed. Rep. of Germany | 252/299.01 |
| 7924831 | 2/1979 | Japan | 252/299.4 |
| 2146787 | 9/1983 | United Kingdom | 350/351 X |

*Primary Examiner*—Teddy S. Gron
*Assistant Examiner*—J. E. Thomas
*Attorney, Agent, or Firm*—Robert Spector

[57] ABSTRACT

Non-crosslinked, branched liquid crystalline organosilicon compounds exhibit the general formula

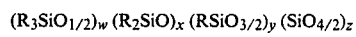

$$(R_3SiO_{1/2})_w (R_2SiO)_x (RSiO_{3/2})_y (SiO_{4/2})_z$$

where at least one R represents a mesogenic (liquid crystal forming) group, the remaning R represent monovalent hydrocarbon or halohydrocarbon radicals, w represents an integer having a value of at least 1, x, y, and z individually represent an integer including zero, the sum of x and y is at least 1 and the sum of w, x, y, and z is from 4 to 50, inclusive.

4 Claims, No Drawings

LIQUID CRYSTALLINE ORGANOSILICON COMPOUNDS

BACKGROUND OF THE INVENTION

1. Field of the Invention

This invention relates to organosilicon compounds exhibiting properties characteristic of liquid crystals. This invention further relates to liquid crystalline organosilicon compounds exhibiting rapidly reversible liquid crystal phase transitions over a wide and relatively low temperature range.

2. Background Information

Many organic compounds exhibit a liquid crystal phase over a particular temperature range. In addition, numerous polymeric organic compounds with a liquid crystal (mesogenic) group in the main chain or side chain exhibit the same effect. There are, however, relatively few examples of polyorganosiloxanes having a liquid crystal phase.

Liquid crystalline polyorganosiloxanes are disclosed in U.S. Pat. No. 4,358,391, issued to Finkelmann et al. on Nov. 9, 1982, U.S. Pat. No. 4,388,453, issued to Finkelmann et al. on June 14, 1983, and U.S. Pat. No. 4,410,570, issued to Kreuzer et al. on Oct. 18, 1983. The polymers of U.S. Pat. No. 4,358,391 contain mesogenic groups bonded as side chains to a linear polydiorganosiloxane. The solid crystal-liquid crystal transition temperature exhibited by these polymers is considerably lower compared to other types of liquid crystalline polymers such as polyacrylic acid esters. In addition, the long period of time required to achieve the reversible transitions from solid crystal to liquid crystal to isotropic liquid makes these transitions substantially irreversible for all practical purposes. The delayed phase transitions may be due to a delay in orientation of the mesogenic group that in turn results from restrictions imposed by the structure of the polyorganosiloxane molecule.

The aforementioned U.S. Pat. No. 4,388,453 discloses three dimensional, crosslinked polyorganosiloxanes containing mesogenic groups within the polymer network. In addition to the disadvantages cited hereinabove in connection with U.S. Pat. No. 4,358,391, the degree of crosslinking must be carefully controlled during polymerization to achieve the required uniform liquid crystalline structure in the final product.

The aforementioned U.S. Pat. No. 4,410,570 teaches eliminating the disadvantage of a slow transition between crystalline and liquid phases that is characteristic of linear polydiorganosiloxanes by employing a cyclic polyorganosiloxane in place of the linear polymer, however this results in an increase in the solid crystal-liquid crystal-isotropic liquid transition temperatures to at least 100° C. The high temperature required to achieve a liquid crystal transition more than outweighs any advantages associated with using polyorganosiloxanes as vehicles for bonding mesogenic groups.

U.S. Pat. No. 4,316,041 discloses silanes of the general formula

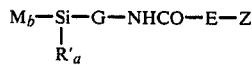

where M is methoxy, ethoxy, chloro or dimethylamino, R' is hydrogen, methyl or ethyl; G is alkylene having from 2 to 4 carbon atoms or arylene of aralkylene, where the arylene and aralkylene radicals contain from 6 to 8 carbon atoms, E is —O— or —NH—; Z is one of four different mesogenic groups; $x$ is from 0 to 2 and $y$ is from 1 to 3. The silanes are prepared by reacting an isocyanatohydrocarbyl-substituted silane with the appropriate mesogenic compound containing a hydroxyl or amino group as a substituent.

An objective of this invention is to provide non-crosslinked liquid crystalline organosilicon compounds that do not exhibit the disadvantages of prior art organosilicon materials.

SUMMARY OF THE INVENTION

The liquid crystalline organosilicon compounds of this invention have a branched structure and contain at least one mesogenic group per molecule. These compounds exhibit rapidly reversible liquid crystal phase transition at relatively low temperatures.

DETAILED DESCRIPTION OF THE INVENTION

This invention provides non-crosslinked liquid crystalline organosilicone compounds of the general formula

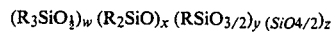

where at least one R represents a mesogenic group that is bonded to silicon by a carbon atom of an alkylene or oxyalkylene radical and the remaining R represent monovalent hydrocarbon or halohydrocarbon radicals; $w$ represents an integer having a value of at least 1; $x$, $y$ and $z$ are individually integers including zero, the sum of $y$ and $z$ is at least 1 and the sum of $w$, $x$, $y$, and $z$ is from 4 to 50, inclusive.

Examples of the monovalent hydrocarbon and halohydrocarbon radicals represented by R in the foregoing formulae include methyl, ethyl, propyl, octyl, vinyl, phenyl and 3,3,3-trifluoropropyl. At least one R per molecule represents a mesogenic group which causes the organosilicon compound to exhibit a nematic phase or cholesteric phase. Preferred examples of mesogenic groups include, but are not limited to the cholesterol group (A), the cyanobiphenyl group (B), substituted benzoate groups (C) and substituted azomethine groups (D) exhibiting the following formulae:

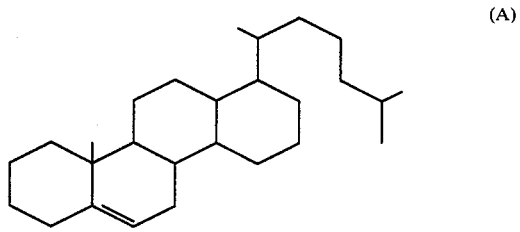

(A)

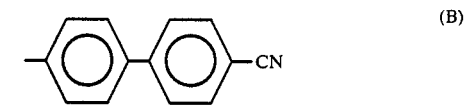

(B)

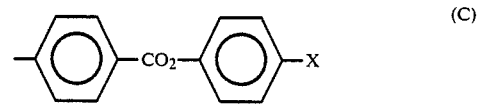

(C)

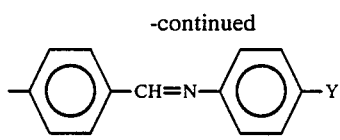 (D)

In these formulae X is a monovalent hydrocarbon radical or alkoxy radical and Y is an alkoxy radical or a nitrile group.

Other examples of mesogenic compounds include cyclohexanecarboxylic acid esters, phenylcyclohexanes, alkoxyphenylpyrimidines, cyclohexylcyclohexanes, azoxy compounds and azo compounds. It will be recognized that any known liquid crystal-orienting compound with a nematic or cholesteric phase can be included in the mesogenic groups represented by R.

The mesogenic groups are bonded to silicon by means of a group that is typically alkylene or oxyalkylene. The bonding group results from an addition reaction between SiH groups present in the organosilicon reactant and an ethylenically unsaturated hydrocarbon radical in the mesogenic organic compound. The unsaturated hydrocarbon radical is preferably allyloxy, $CH_2=CHCH_2O-$.

To have a branched structure, the liquid crystalline organosilicon compound must contain at least one $RSiO_{3/2}$ unit or $SiO_{4/2}$ unit in each molecule. Both units may be present simultaneously. To terminate all or a portion of these units, at least one $R_3SiO_{1/2}$ unit per molecule is required. One or more $R_2SiO$ unit may also be present. As disclosed hereinbefore, at least one of the R groups must be mesogenic. Preferably, one of the R groups in the $R_3SiO_{\frac{1}{2}}$ unit is a mesogenic group. The selection of a particular mesogenic group determines whether the organosilicon compound exhibits a cholesteric or nematic phase. One or more types of mesogenic groups can be present in one molecule.

The reason for limiting the total number of siloxane units to from 4 to 50 is that a minimum of 4 units is required for a branched structure. A lengthy transition time for the liquid crystal phase is required when the organosilicon compound contains more than 50 siloxane units.

A preferred class of liquid crystalline organosilicon compounds of this invention exhibits the general formula

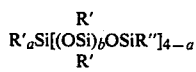

where each R' is individually selected from the group consisting of monovalent hydrocarbon and monovalent halohydrocarbon radicals, R" is a mesogenic group as defined hereinbefore for R, a is 0 or 1 and b is an integer from 0 to 10, inclusive. Most preferably R' is methyl, phenyl or 3,3,3-trifluoropropyl.

Various methods can be used to produce the liquid crystalline organosilicon compounds of this invention. One preferred method involves hydrosilylation of an allyloxy group-containing liquid crystalline organic compound by reacting it with a branched organosilicon reactant containing at least 3 silicon-bonded hydrogen atoms per molecule in the presence of a platinum catalyst.

The organosilicon reactant can be prepared by the simultaneous co-hydrolysis and condensation of mixtures of silanes containing silicon-bonded halogen and/or alkoxide groups. The silanes provide the siloxane groups shown in the foregoing formulae. One of the silanes contains at least one silicon-bonded hydrogen atom per molecule, and can be, for example, methyldichlorosilane, dimethylchlorosilane, methyldimethoxysilane, phenylmethylchlorosilane or dimethylethoxysilane. This silane is co-hydrolyzed with a halosilane such as methyltrichlorosilane, dimethylchlorosilane, trimethylchlorosilane, tetrachlorosilane, ethyltrichlorosilane and propyltrichlorosilane. The chlorine atoms in any of the preceding silanes can be replaced by alkoxy groups.

At least one silane containing three or four halogen atoms or alkoxy groups must be present in the co-hydrolysis reaction mixture to produce a branched structure in the SiH-containing organosilicon reactant. Methyltrichlorosilane and tetrachlorosilane are preferred for this purpose.

Examples of the SiH-containing branched organosilicon reactants of this invention are tetrakis(dimethylsiloxy)silane, tetrakis(diethylsiloxy)silane, tetrakis(methylphenylsiloxy)silane, methyltris(dimethylsiloxy)silane, phenyltris(dimethylsiloxy)silane and compounds containing a plurality of siloxane units such as

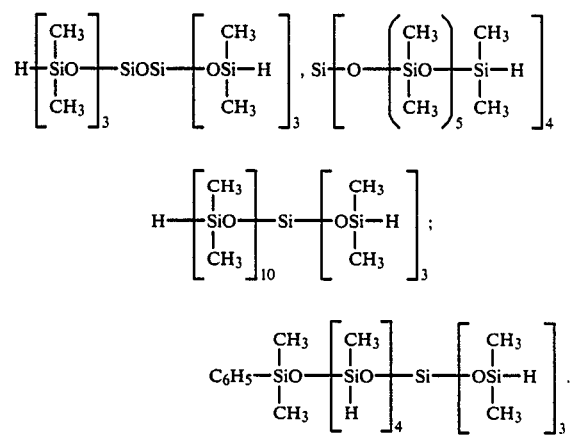

From the viewpoints of ease of production and desirable properties, tetrakis(dimethylsiloxy)silane and methyltris(dimethylsiloxy)silane are preferred organosilicon reactants.

The branched liquid crystalline organosilicon compound of the invention can be prepared by dissolving the SiH-containing organosilicon reactant and mesogenic group-substituted unsaturated compound in a common solvent such as toluene, diethyl ether or tetrahydrofuran. The resultant solution is stirred at temperatures of from room temperature to the reflux temperature of the solvent (about 110° C. for toluene). A platinum catalyst such as chloroplatinic acid hexahydrate or a platinum-ethylene complex is added in an amount equivalent to from 10 to 100 ppm of platinum metal, based on the total weight of the reactants. When the unsaturated group is allyloxy, the liquid crystalline organosilicon compound is produced by an addition reaction in accordance with the following equation:

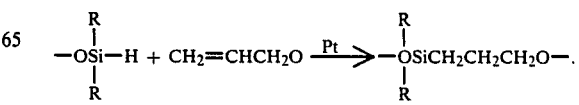

To ensure a complete reaction, the molar ratio of vinyl radicals to silicon-bonded hydrogen atoms is preferably from 1.01 to 1.1. The liquid crystalline organosilicon compound is isolated by removing the solvent after the reaction is substantially complete.

The liquid crystalline organosilicon compounds of this invention can be used individually or in combination with other liquid crystalline organosilicon compounds or with liquid crystalline organic compounds. The compositions can also include conventional additives such as colorants and dyestuffs.

The following examples describe preferred embodiments of the present liquid crystalline organosilicon compounds and methods for their preparation. The examples should not be interpretted as limiting the scope of the present invention as defined in the accompanying claims. All parts and percentages are by weight unless otherwise specified.

EXAMPLE 1

A mixture containing 0.1 mol (16.15 g) methyltrichlorosilane and 0.3 mol (22.2 g) dimethylchlorosilane was added drop-wise to a mixture of 200 cc petroleum ether and 500 cc of an ice/water mixture. After separating the water, the petroleum ether layer was dried over sodium sulfate and the petroleum ether removed by distillation. Fractional distillation of the residue produced a 60% yield of methyltris(dimethylsiloxy)silane (A), $$CH_3Si\left[\begin{array}{c} CH_3 \\ | \\ OSiH \\ | \\ CH_3 \end{array}\right]_3.$$

The product was collected at 60° C. under a pressure of 2.5 kPa. Using a differential scanning calorimeter (DSC), the melting point was −155° C.

1.23 g (4.59 mmol) (A) and 5.0 g (15.15 mmol) p-allyloxy-p'-diphenylbenzoate

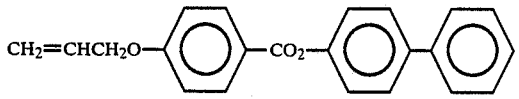

were dissolved in 50 cc dry toluene and the resultant solution diluted with isopropyl alcohol. An amount of $H_2PtCl_6 \cdot 6H_2O$ equivalent to 10 ppm of platinum metal was added to the solution and the resultant mixture was reacted for 3 hours at reflux temperature (110° C.). The solvent was then removed under reduced pressure to obtain a milky white solid. Infrared and nuclear magnetic resonance (NMR) spectra confirmed the identity of the product as methyltris[γ-(p-diphenylbenzoato)-propyldimethylsiloxy]silane.

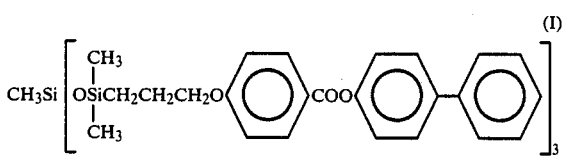

Observation of the liquid crystalline phase through a polarizing microscope reveals the presence of a nematic phase at between 70° and 75° C. which is rapidly reversible in response to temperature variation. The product was thereby confirmed to be a liquid crystalline organosilicon compound in accordance with the present invention.

EXAMPLE 2

0.1 mol (17 g) tetrachlorosilane and 0.4 mol (37.8 g) dimethylchlorosilane were cohydrolyzed and condensed using the procedure described hereinbefore in Example 1. The product, tetrakis(dimethylsiloxy)silane

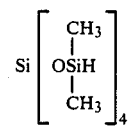

was collected at 52° C. under a pressure of 0.8 kPa in 55% yield. Using DSC, the melting point is measured at −108° C. 1.13 g (3.44 mmol) of this silane and 5.0 g (15.14 mmol)p-allyloxy-p'-diphenylbenzoate were then reacted using the procedure described hereinbefore in Example 1. The infrared and NMR spectra confirmed the identity of the product as tetrakis[γ-(p-diphenylbenzoatopropyldimethylsiloxy]silane.

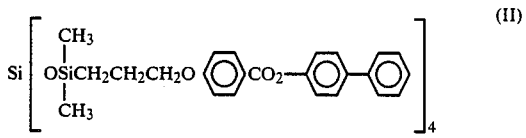

Observation of this organosilicon compound through a polarizing microscope confirmed the presence of a liquid crystalline compound of this invention exhibiting a nematic phase between 62° C. and 83° C. which is rapidly reversible in response to temperature change.

EXAMPLE 3

1.0 g (3.05 mmol)tetrakis(dimethylsiloxy)silane and 6.3 g (13.4 mmol) cholesteryl allyl carbonate were reacted using the procedure described hereinbefore in Example 1. The infrared and NMR spectrum confirmed the identity of the product as tetrakis[γ-(cholesteryl carbonate)propyldimethylsiloxy]silane.

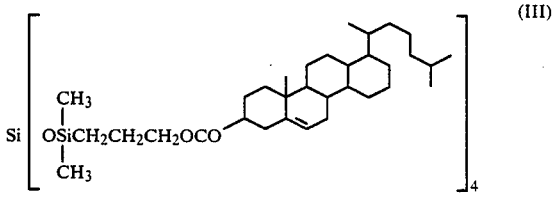

This product is thick and viscous at room temperature, and exhibited the characteristic red/green color of a cholesteric phase. The material converted to a transparent isotropic liquid upon heating to 50° C. and reverted to the characteristic red/green color after cooling to room temperature.

EXAMPLES 4 AND 5 14.0 mmol of each of the compounds with the following formulae as the unsaturated group-containing liquid crystalline compound were individually reacted with 3.2 mmol tetrakis(dimethylsiloxy)silane of Example 2 under the conditions described hereinbefore in Example 1.

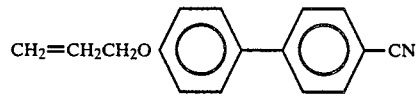

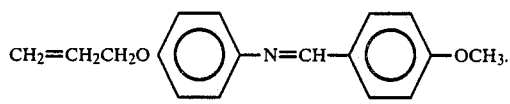

The infrared and NMR spectra confirmed the identity of the products as the following compounds of this invention:

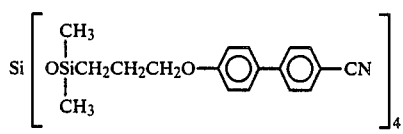

and

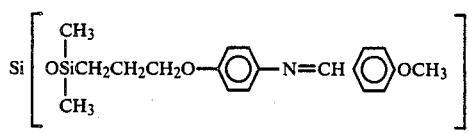

Based on polarizing microscopic observation, it was found that (IV) and (V) exhibited waxy nematic phases at room temperature. Conversion to an isotropic liquid occurs at 70° C. for (IV) and 35° C. for (V). These phase transitions were rapidly reversible in response to temperature.

EXAMPLE 6

0.44 mol (98.6 g) of α-hydroxyhexamethyltrisiloxane

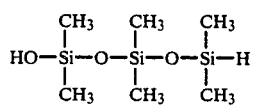

was slowly dripped into 0.1 mol (17 g) tetrachlorosilane SiCl$_4$, 500 cc petroleum ether and 0.44 mol (40 g) pyridine. The liquid was cooled by an ice/water mixture to keep the temperature below 50° C. Following completion of the addition, the pyridine hydrochloride byproduct was filtered off and the filtrate was transferred to a separatory funnel, washed with water and dried over sodium sulfate. The sodium sulfate was then filtered off and the solvent was distilled under reduced pressure to provide a 62 weight % yield of tetrakis(hexamethyltrisiloxy)silane (B),

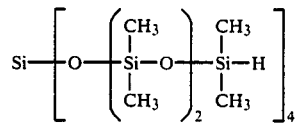

1.2 g (5.35 mmol) B, 7.77 g (23.54 mmol) p-allyloxy-p'diphenylbenzoate and 40 cc dry toluene were mixed. A solution of chloroplatinic acid in 2-ethylhexanol was added in an amount equivalent to a platinum metal concentration of 10 ppm. The resultant mixture was heated at 100° C. for 5 hours. The solvent was then removed under reduced pressure and methanol added to the concentrated solution. The insoluble white solid was filtered and dried under reduced pressure at room temperature. The following structure was confirmed by NMR and IR spectra:

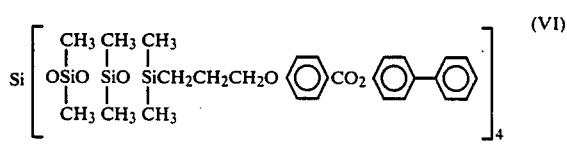

Using the polarizing microscope, the compound with formula (VI) is confirmed to be a liquid crystalline organosilicon compound with a nematic phase between 55° C. and 62° C. which is reversible in response to temperature.

COMPARISON EXAMPLES 1 AND 2

Methyldichlorosilane CH$_3$(H)SiCl$_2$ was hydrolyzed and condensed as described in Example 1 to obtain tetramethylcyclotetrasiloxane (bp 135° C.).

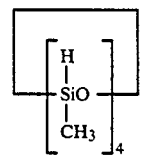

Using DSC, the melting point of the cyclic siloxane was determined to be −72° C. Using the same procedure as described in Example 1, this cyclic siloxane and p-allyloxy-p'diphenylbenzoate or cholesteryl allyl carbonate were reacted to yield compounds corresponding to formulae (VII) and (VIII), respectively.

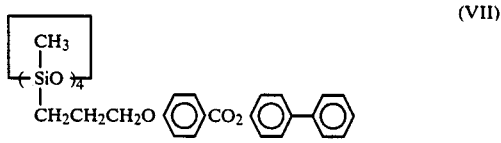

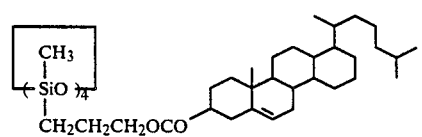

Cyclic siloxane (VII) exhibits a nematic phase between 134° C. and 160° C. Cyclic siloxane (VIII) exhibits a cholesteric phase between 101° C. and 107° C. Compared with the liquid crystalline organosilicon compounds (II) and (III) of this invention, these liquid crystal phase temperatures are at least 50° C. higher.

It is apparent from the foregoing examples and comparative crystalline organosilicon compounds of this invention exhibit a liquid crystal phase at a lower temperature relative to the compounds of the comparative examples. At the same time, they show a rapidly reversible phase change in response to temperature changes. Liquid crystalline materials are currently used in various fields. The liquid crystalline compounds of this invention are particularly useful as temperature measuring devices for non-destructive testing of materials, utilizing the color change exhibited by the compounds in response to temperature change, and in display devices utilizing electro-optical effects.

That which is claimed is:

1. A non-crosslinked liquid crystalline organosilicon compound of the general formula $$(R_3SiO_{\frac{1}{2}})_w (R_2SiO)_x (RSiO_{3/2})_y (SiO_{4/2})_z$$

where at least one R present on at least one of the $R_3SiO_{\frac{1}{2}}$ units represents a mesogenic group that exhibits a nematic or cholesteric phase and is bonded to silicon by a carbon atom of an alkylene or oxyalkylene radical and the remaining R are individually selected from the group consisting of methyl, phenyl and 3,3,3-trifluoropropyl radicals, $\underline{w}$ represents an integer having a value of at least 1, $\underline{x}$, $\underline{y}$ and $\underline{z}$ are individually integers including 0, the sum of $\underline{y}$ and $\underline{z}$ is at least 1 and the sum of $\underline{w}$, $\underline{x}$, $\underline{y}$ and $\underline{z}$ is from 4 to 50, inclusive.

2. The organosilicon compound of claim 1 where the compound exhibits a formula selected from the group consisting of

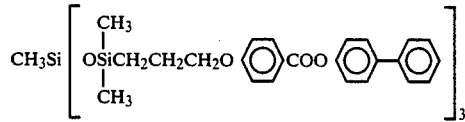

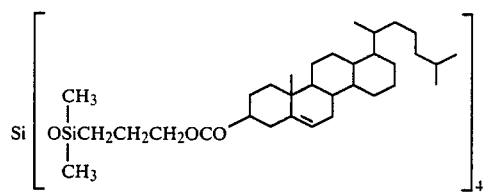

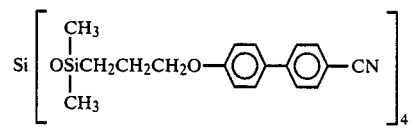

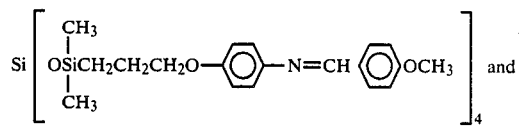

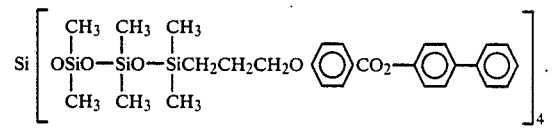

3. An organosilicon compound according to claim 1 exhibiting a general formula $$R'_aSi[(OSi)_bOSiR'']_{4-a},$$
with R' R' / R' R' where each R' is individually selected from the group consisting of methyl, phenyl and 3,3,3,-trifluoropropyl radicals, R" represents said mesogenic group and is bonded to silicon by means of a carbon atom that is part of an alkylene or alkenyloxy radical, a is 0 or 1 and b represents an integer from 0 to 10, inclusive.

4. An organosilicon compound according to claim 3 where said compound exhibits the formula $$R'_aSi[(OSi)_bOSiR'']_{4-a},$$

R' is methyl and the carbon atom bonding R" to silicon is part of an alkyleneoxy radical.

* * * * *